US007459068B2

(12) United States Patent
Nordman et al.

(10) Patent No.: US 7,459,068 B2
(45) Date of Patent: *Dec. 2, 2008

(54) MULTI-CAPILLARY ELECTROPHORESIS APPARATUS

(75) Inventors: Eric S. Nordman, Palo Alto, CA (US); Miho Ozawa, Ibaragi (JP); Masaya Kojima, Ibaragi (JP); Ryoji Inaba, Ibaragi (JP); Yoshitaka Kodama, Ibaragi (JP); Motohiro Yamazaki, Ibaragi (JP)

(73) Assignee: Applied Biosystems Inc., Foster City, CA (US)

( * ) Notice: Subject to any disclaimer, the term of this patent is extended or adjusted under 35 U.S.C. 154(b) by 54 days.

This patent is subject to a terminal disclaimer.

(21) Appl. No.: 10/309,729

(22) Filed: Dec. 4, 2002

(65) Prior Publication Data
US 2003/0127328 A1 Jul. 10, 2003

Related U.S. Application Data

(63) Continuation-in-part of application No. 10/245,492, filed on Sep. 18, 2002, now abandoned.

(30) Foreign Application Priority Data
Dec. 4, 2001 (JP) ............................. P2001-370349

(51) Int. Cl.
*G01N 27/26* (2006.01)
*G01N 27/447* (2006.01)
(52) U.S. Cl. .................... 204/451; 204/452; 204/455; 204/601; 204/603; 204/605
(58) Field of Classification Search ......... 204/451–455, 204/601–605
See application file for complete search history.

(56) References Cited

U.S. PATENT DOCUMENTS 4,253,515 A * 3/1981 Swiatosz .................... 165/61

(Continued)

FOREIGN PATENT DOCUMENTS

GB 2312505 A 10/1997

(Continued)

OTHER PUBLICATIONS

G.A. Ross, "Voltage pre-conditioning technique for optimisation of migration-time reproducibility in capillary electrophoresis", J. Chromatogr. A. 718, 444-447. (1995).*

(Continued)

*Primary Examiner*—Nam X Nguyen
*Assistant Examiner*—Jeffrey Barton
(74) *Attorney, Agent, or Firm*—Kilyk & Bowersox, P.L.L.C.

(57) ABSTRACT

A multi-capillary electrophoresis apparatus is provided for reducing errors during analysis caused by fluctuations in electrophoresis time among plural capillaries of the apparatus. The multi-capillary electrophoresis apparatus can contain a multi-capillary array that has a separation medium filled therein for isolating a sample. A detector component can be provided at a position remote from a sample injecting end of the array for acquiring information from the sample. A buffer container can be provided for holding a buffer solution into which the sample injecting end can be immersed. One or more temperature controlling component devices can be arranged for controlling a temperature of the buffer solution, of the detector component, or of both the buffer solution and the detector component.

39 Claims, 10 Drawing Sheets

U.S. PATENT DOCUMENTS

| | | | |
|---|---|---|---|
| 5,021,646 A | 6/1991 | Weinberger et al. | 250/227.11 |
| 5,066,382 A | 11/1991 | Weinberger | |
| 5,085,757 A * | 2/1992 | Karger et al. | 204/603 |
| 5,413,686 A * | 5/1995 | Klein et al. | 204/603 |
| 5,423,966 A * | 6/1995 | Wiktorowicz | 204/453 |
| 5,814,524 A | 9/1998 | Walt et al. | |
| 5,833,827 A | 11/1998 | Anazawa et al. | 204/603 |
| 5,885,430 A * | 3/1999 | Kernan et al. | 204/453 |
| 5,938,908 A | 8/1999 | Anazawa et al. | 204/603 |
| 5,993,634 A | 11/1999 | Simpson et al. | 204/612 |
| 6,017,434 A | 1/2000 | Simpson et al. | 204/612 |
| 6,387,234 B1 * | 5/2002 | Yeung et al. | 204/451 |
| 6,572,752 B1 | 6/2003 | Maeshima et al. | |
| 6,635,164 B1 * | 10/2003 | Anazawa et al. | 204/603 |
| 2001/0040094 A1 | 11/2001 | Inaba et al. | 204/603 |
| 2003/0127328 A1 | 7/2003 | Nordman et al. | |

FOREIGN PATENT DOCUMENTS

| | | | |
|---|---|---|---|
| JP | 04-175655 | | 6/1992 |
| JP | 06-138037 | | 5/1994 |
| JP | 07-020090 | * | 1/1995 |
| JP | 2000-131279 | | 5/2000 |
| JP | 2001-324473 | | 10/2001 |
| WO | WO 95/21378 | * | 8/1995 |

OTHER PUBLICATIONS

Lu et al., *Optimization of Excitation and Detection Geometry for Multiplexed Capillary Array Electrophoresis of DNA Fragments, Applied Spectroscopy*, 49/5, pp. 605-609, (May 1995).

International Search Report for International Application No. PCT/US02/38811 dated Feb. 14, 2003.

Exhibit A—Labeled Photograph of inside of Applied Biosystems' ABI Prism® 3100 Genetic Analyzer, on sale more than one year before Sep. 18, 2002.

\* cited by examiner

MULTI-CAPILLARY ELECTROPHORESIS APPARATUS

CROSS REFERENCE TO RELATED APPLICATION

The present application is a Continuation-In-Part application of U.S. patent application Ser. No. 10/245,492 filed Sep. 18, 2002, now abandoned, entitled "Multi-Capillary Electrophoresis Apparatus" in the name of Miho Ozawa et al., which claims a priority benefit from Japanese Patent Application No. P2001-370349, filed Dec. 4, 2001, all of which are incorporated herein in their entireties by reference. The subject matter of the present application was developed under a joint research agreement between Applera Corporation and Hitachi High-Technologies Corporation. Applera Corporation changed its name to Applied Biosystems Inc. in 2008.

BACKGROUND

The present disclosure relates to a multi-capillary electrophoresis apparatus having a multi-capillary array formed with plural capillaries each having a sample and a separation medium filled therein. More particularly, the present disclosure relates to an apparatus that can suppress measurement fluctuations upon analysis, improve performance, and reduce run-to-run variability.

In recent years, a capillary electrophoresis apparatus including a capillary tube having an electrophoretic medium (separation medium) filled therein, such as a high-polymer polymer and a polymer solution, has been developed, as disclosed in Japanese Laid-open Patent Publication JP-A 6-138037. This capillary electrophoresis apparatus has high heat dissipation capacity and can be applied with a high voltage, in comparison to a conventional slab polymer electrophoresis apparatus. Therefore, it has the advantage that electrophoresis can be carried out at a high rate.

FIG. 10 shows a schematic structure of a known capillary electrophoresis apparatus. As shown in FIG. 10, the capillary electrophoresis apparatus B has a capillary component 103, a temperature regulated chamber 105, a detector component 107 and a buffer container 111.

The capillary component 103 is formed with plural capillaries 103a. The buffer container 111 is filled with a buffer solution 111a. A sample and a separation medium for separating the sample are filled into the capillaries 103a. Ends 103b of the capillaries 103a are immersed in the buffer solution 111a. The other ends 103c of the capillaries 103a are also immersed in, for example, a buffer solution.

The detector component 107 includes a retaining component 107b for retaining the capillaries 103a. The detector component 107 is housed in the retaining component 107b and a cover member 108. A high voltage is applied between the ends 103b and the other ends 103c of the capillaries 103a, whereby the sample is electrophoresed in the separation medium. The sample thus separated by electrophoresis is detected in the detector component 107 with an optical mechanism. The retaining component 107b has a window component 107c for capturing fluorescence excited by the optical mechanism.

In the capillary electrophoresis apparatus, Joule heat is generated upon applying a high voltage between both ends 103b and 103c of the capillary 103a. As a result, air dissolved in the liquid of the separation medium forms bubbles upon exposure to this increase in temperature to raise the resistance of the separation medium. When the separation medium has a high resistance, the electrophoresis migration velocity is lowered to cause adverse affects, such as deterioration in resolution power of the sample.

SUMMARY

According to various embodiments, a multi-capillary electrophoresis apparatus is provided having a multi-capillary array containing plural capillaries in which temperature fluctuations can be reduced. According to various embodiments, adverse affects such as fluctuations in the electrophoresis time can be reduced.

According to various embodiments, a multi-capillary electrophoresis apparatus can include a multi-capillary array filled with a separation medium useful for isolating a sample. The multi-capillary array can have a sample injecting end arranged on one end thereof and a detector component, for acquiring information from the sample, at a position remote from the sample injecting end. A voltage applying component can be provided for applying a voltage to an electrification path containing the sample injecting end and the detector component. According to various embodiments, a temperature regulated chamber can contain substantially all of the multi-capillary array except for the sample injecting end. A buffer container can contain a buffer solution into which the sample injecting end is immersed. A temperature controller can control a temperature of the buffer solution. According to various embodiments, a temperature regulated chamber can contain substantially all of the multi-capillary array except for the detector component. According to various embodiments, a temperature controller can control a temperature of the detector component. According to various embodiments, a temperature controller can control a temperature of the buffer solution and a temperature of the detector component. According to various embodiments, some or all of these features are included in a multi-capillary electrophoresis apparatus.

According to various embodiments, the temperature of the capillaries in the array can be controlled by the temperature controller and fluctuations in temperature of the separation medium can be reduced and results of an analysis can be improved.

BRIEF DESCRIPTION OF THE DRAWINGS

The invention may be more fully understood with reference to the accompanying drawing figures and the descriptions thereof. Modifications that would be recognized by those skilled in the art are considered a part of the present invention and within the scope of the appended claims.

DETAILED DESCRIPTION OF CERTAIN EMBODIMENTS

Figure 1:
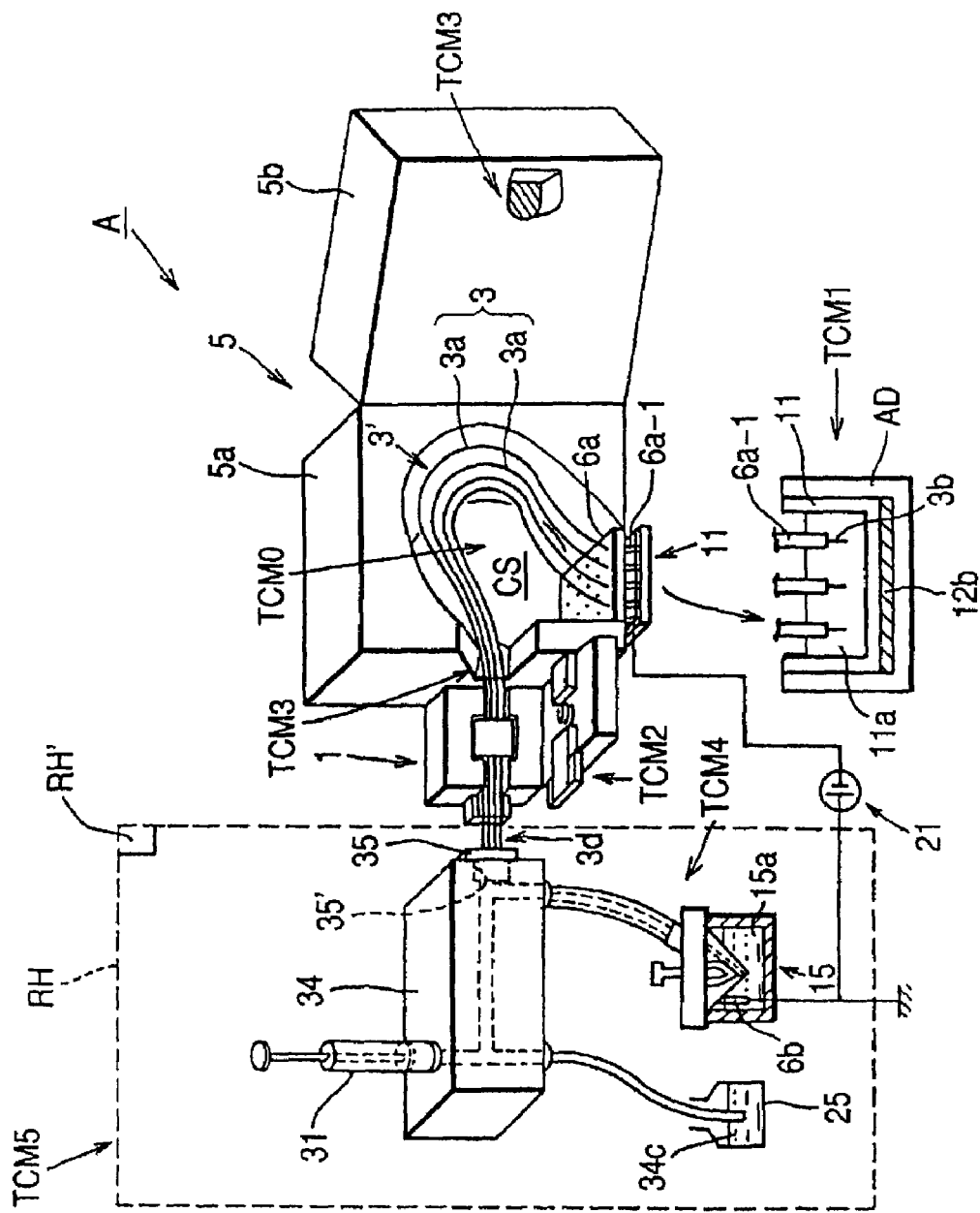
FIG. 1 illustrates an overall structure of a multi-capillary electrophoresis apparatus according to various embodiments, and also illustrates the structure of temperature controlling parts.

According to various embodiments, fluctuations in analytical results among capillaries of a multi-capillary electrophoresis device array having plural capillaries can be suppressed by controlling the temperature of the buffer solution in which the sample injecting end of the capillaries is immersed. The temperature can be controlled with, for example, a heater. According to various embodiments, fluctuations in analytical results among the plural capillaries can be suppressed by controlling the temperature of the detector component. In particular, by controlling the temperature in the vicinity of the detecting component of the capillaries to be inspected, erroneous fluctuations in the results can be suppressed.

According to various embodiments, in order to prevent local generation of heat in capillaries the capillaries can be placed in a temperature regulated chamber whereby the electrophoresis is carried out under the condition where the temperature of a portion of the capillary is maintained constant.

According to various embodiments, it is difficult to place the entire length of the capillaries in a temperature regulated chamber. For example, in the device shown in FIG. 10, the end 103b forming the sample injecting end for injecting the sample, and the detector component 107 for detecting the sample with an optical mechanism, are not contained within the temperature regulated chamber 105. According to various embodiments, it is recognized that it is difficult to place the sample injecting end 103b in the temperature regulated chamber because this end must access samples at the bottom of tubes or wells. Moreover, according to various embodiments, it is recognized that the samples can be degraded by long term exposure to the chamber temperature and need to be customer accessible during electrophoresis. Consequently, incorporating the samples into the temperature regulated chamber of such a device is avoided. According to various embodiments, it is recognized that the detection zone of such a device can be excluded from the temperature regulated chamber due to the size of the optics and problems associated with heating various optical components.

According to various embodiments, during operation, the capillaries can be in the sample well for a short time. After injection, the capillaries can be rinsed and can be moved to a thermally unregulated buffer chamber for electrophoresis. To ensure adequate denaturation, additives, such as Urea, can be incorporated in the separation medium.

According to various embodiments, the temperature of the separation medium can be maintained at a temperature different from the environment. The ideal temperature can be dependent upon the application and the separation medium. For example, in DNA analysis, the DNA can be maintained in a denatured (single strand) condition. This can be done by conducting the electrophoresis at elevated temperatures and by using denaturants (such as Urea) in the separation medium. In some DNA applications, the DNA can be denatured (double stranded), and lower operating temperatures can be used for such applications.

According to various embodiments, measurement fluctuations of fragment size (commonly measured as standard deviation of base size) can be reduced by ensuring that the temperature of the separation medium is held constant. Increasing the temperature of the separation medium can be used to reduce the standard deviation by insuring more complete denaturation.

According to various embodiments, it is difficult to place the entire length of the capillaries in the temperature regulated chamber. For example, in the device of FIG. 10, the end 103b forming a sample injecting end for injecting the sample and the detector part 107 for detecting the sample with an optical means are not placed in the temperature-regulated chamber 105.

Figure 10:
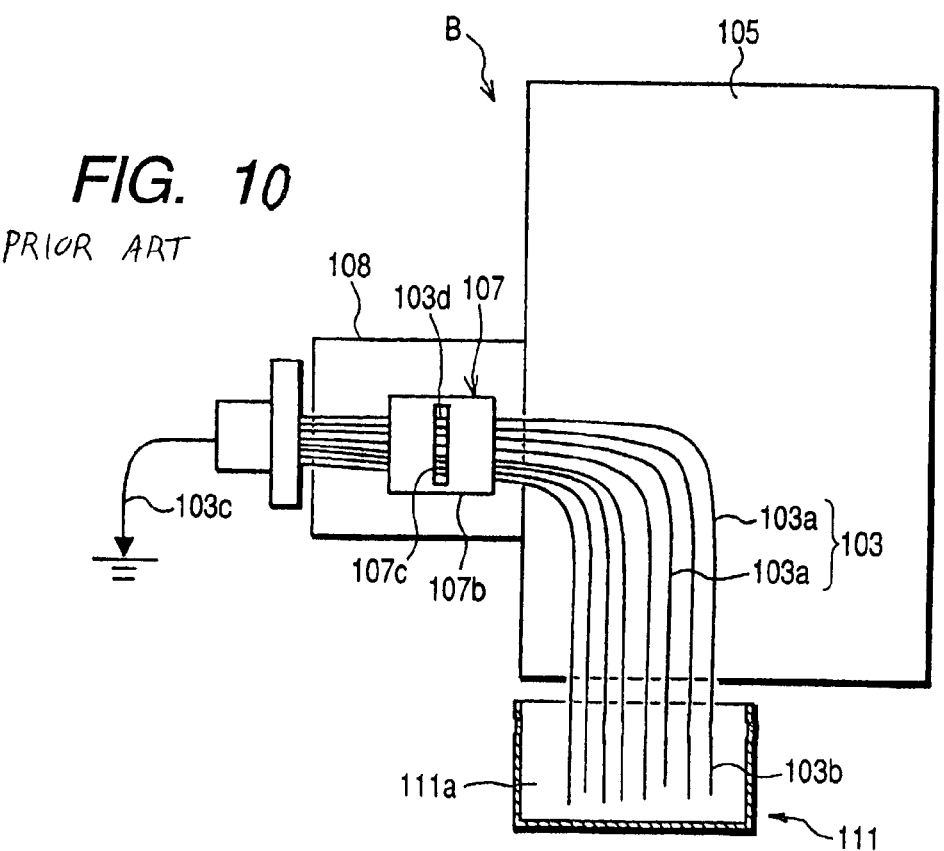
FIG. 10 illustrates a schematic drawing of a known multi-capillary electrophoresis apparatus.

According to various embodiments, it is recognized that a light emission component that emits, for example, laser light, to the detector component 107 can be provided in the electrophoresis apparatus as shown in FIG. 10. A CCD image sensor (or a CCD camera having the same) can be provided for receiving the light emitted by the fluorescent dyes after being excited in the detecting component 103d. Thermal noise of the CCD image sensor can be increased by the influence of heat.

In order to reduce the thermal noise, it is desirable that the CCD image sensor be arranged in the vicinity of the detector component 107 and that it be maintained at a low temperature as long as possible. Accordingly, it is recognized that it is not preferable that both the detector component 107 and the CCD image sensor be placed in the temperature regulated chamber 105.

According to various embodiments, it is recognized that in the detector component 107, the temperature of the separation medium in the radial direction of the capillaries is likely to fluctuate among the plural capillaries. The temperature of the separation medium in the electrophoresis components that are outside of the temperature regulated chamber will change when the room temperature varies. It is recognized that this fluctuation will cause adverse affects to the electrophoretic separation. In addition, increasing the temperature of the separation medium will also reduce the fluctuations by insuring more complete denaturation.

An exemplary multi-capillary electrophoresis apparatus according to various embodiments will be described with reference to FIG. 1 to FIG. 9.

FIG. 1 is a diagram showing the overall structure of the multi-capillary electrophoresis apparatus according to various embodiments.

As shown in FIG. 1, a multi-capillary electrophoresis apparatus A according to various embodiments can have a multi-capillary array 3 including plural capillaries 3a installed in a container portion CS of a temperature regulated chamber 5.

Figure 4A:
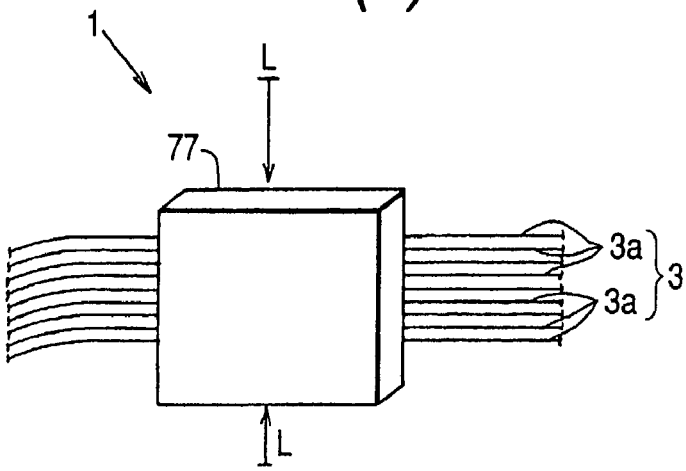
FIGS. 4(a) to 4(c) illustrate a structure of the detector component of the multi-capillary electrophoresis apparatus according to various embodiments.
Figure 4B:
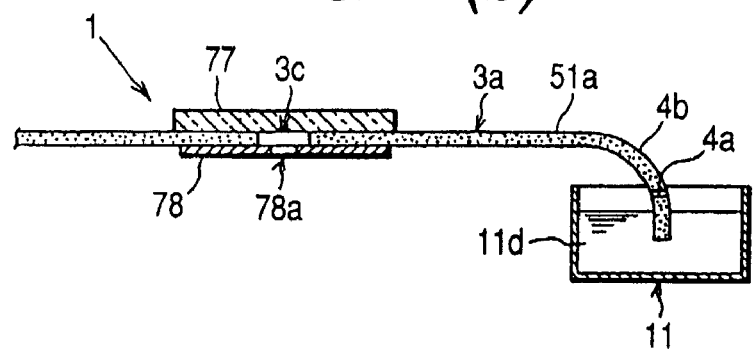

According to various embodiments, a sample 4a, (FIG. 4(b)) containing, for example, specimens of DNA molecules, and a separation medium 4b functioning as a medium for isolating the DNA molecules in the sample 4a, can be introduced into the capillaries 3a. The separation medium 4b can be constituted with, or include, for example, a polymer in a gel form (FIG. 2(c)).

According to various embodiments, a DNA fragment sample contained in the sample 4a can be distinguished by labeling a primer or a terminator with a fluorescent substance using the Sangar dideoxy method. The DNA fragment sample thus labeled with a fluorescent substance can be detected utilizing an optical mechanism described later.

According to various embodiments, one end of the capillary 3a can constitute an injecting end 3b for injecting the sample 4a by protruding from a bottom of the temperature regulated chamber 5. The injecting end 3b can be immersed in a buffer solution 11a. The buffer solution 11a can be contained in a buffer container 11. An electrode 6a can be mounted on the injecting end 3b of the capillary 3a.

According to various embodiments, the other end of the capillary 3a can protrude from a side of the temperature regulated chamber 5 and through a detector component 1 capable of acquiring information from the sample 4a. A plurality of these end parts 3d can be packed at a capillary fixing part 35. End parts 3d can be connected to an upper polymer block 34. The upper polymer block 34 can be connected to a buffer container 15 having a buffer solution 15a filled therein, a polymer storage container 25 having a polymer, for example, separation medium, 34c filled therein, and a syringe 31.

As shown with a broken line, a temperature regulated region RH can be provided and can contain at least one of the upper polymer block 34, the buffer container 15, and the syringe 31.

A multi-capillary electrophoresis apparatus A according to various embodiments can have at least one temperature controller for controlling the temperature controlling part(s) TCM1 to TCM5, in addition to a temperature controlling part TCM0. Temperature controlling part TCM0 can be provided in an ordinary multi-capillary electrophoresis apparatus for controlling the temperature of the capillaries 3a with the temperature regulated chamber 5.

A multi-capillary electrophoresis apparatus according to various embodiments will be described in detail below with a focus on the temperature controlling parts.

Figure 2A:
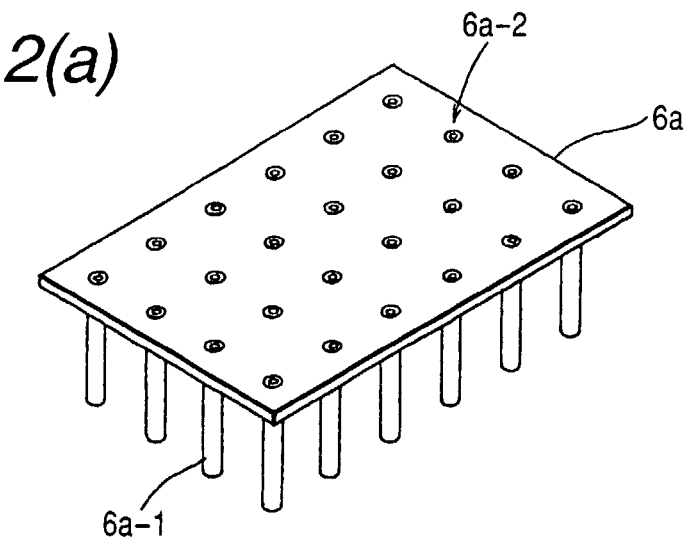
FIGS. 2(a) and 2(b) illustrate a structure of an electrode of the multi-capillary electrophoresis apparatus according to various embodiments.

Several temperature controlling parts will be described with reference to FIGS. 1 to 3(b). The end of the sample injecting end 3b of each capillary 3a can be immersed in the buffer solution 11a. The buffer solution 11a can be provided in the buffer container 11. As shown in FIG. 2(a), a sample injecting end electrode assembly 6a is formed by pressing stainless-steel tubes 6a-1 into a metallic plate 6a-2.

Figure 2B:
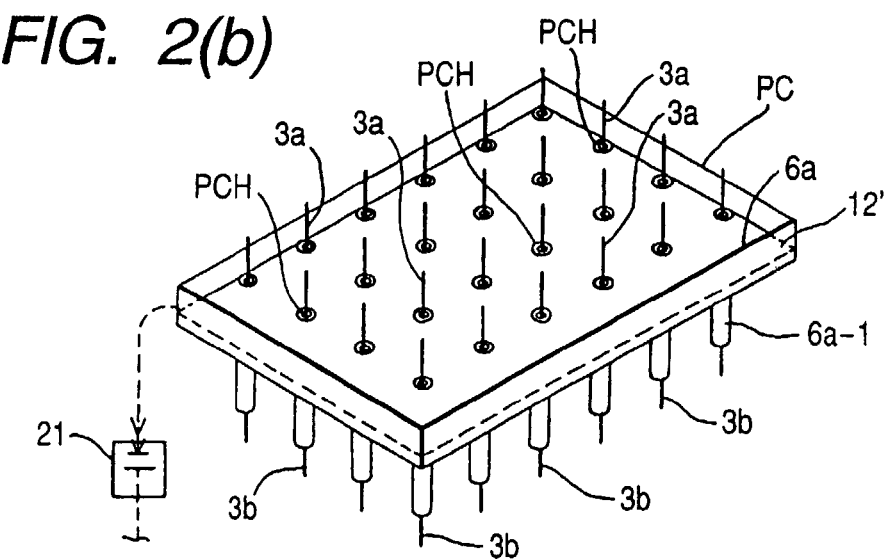
Figure 2C:
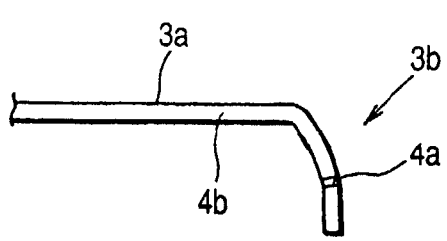
FIG. 2(c) illustrates a structure of a capillary in the vicinity of a sample injecting end inserted in the electrode according to various embodiments.
Figure 3A:
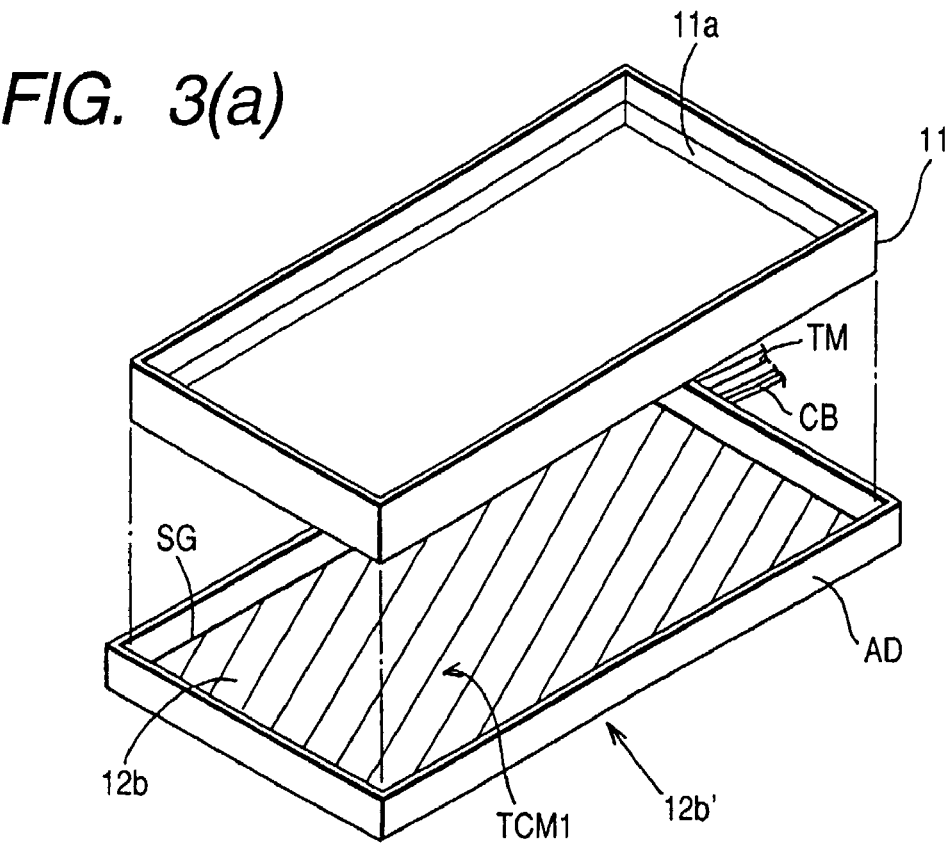
FIGS. 3(a) and 3(b) illustrate the structures of the buffer container and a temperature controlling part installed therein for controlling the temperature of the buffer solution in the multi-capillary electrophoresis apparatus according to various embodiments.
Figure 3B:
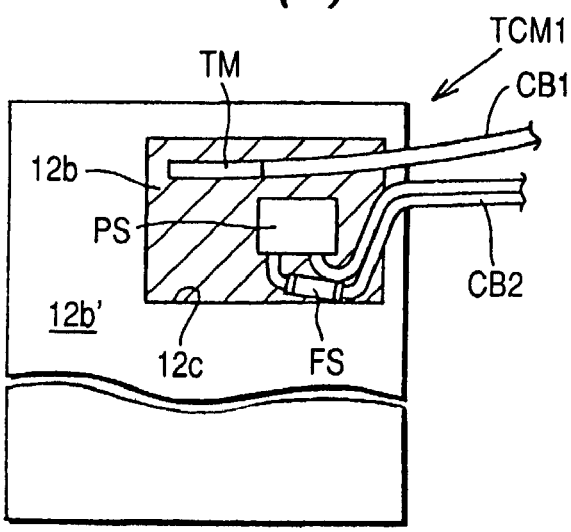

As shown in FIG. 2(b), according to various, embodiments, the sample injecting end 3b can be inserted into the stainless-steel tubes 6a-1 to integrate the sample injecting end 3b and the electrode 6a. A negative electrode from the direct current power supply 21 (FIG. 1) can be connected to the electrode assembly 6a through an electrode (not shown in the figure) of the apparatus. As shown in FIG. 2(c), the separation medium 4b can be filled in the capillaries 3a, and the sample 4a can be introduced in the vicinity of the sample injecting end 3b.

As shown in FIG. 1, the sample injecting end 3b and the electrode assembly 6a can be immersed in the buffer solution 11a filled in the buffer container 11. The buffer solution 11a can be prepared with, for example, sodium ion and TAPS (N-tris(hydroxymethyl)methyl-3-aminopropanesulfonic acid).

The buffer container 11 can be installed in an adapter AD having an opening on an upper part thereof. The adapter AD can have a rubber heater 12 laid on an inner bottom surface thereof.

According to various embodiments, the rubber heater 12b and the adapter AD can be waterproofed by sealing with silicone rubber SG. An opening 12c can be formed on an outer bottom surface 12b' of the adapter AD. A thermistor (temperature monitor) TM can be attached to the back surface of the rubber heater 12b exposed from the opening 12c, and a first cable CB1 can be connected to the thermistor TM. Furthermore, a second cable CB2 can be connected to a power supply PS for the heater and a fuse FS can be attached to the back surface of the rubber heater 12b.

According to various embodiments, the temperature within the surface of the buffer container 11 in contact with the rubber heater 12b can be made constant by using the rubber heater 12b. Maintenance operations, such as replacement of the buffer, can be conveniently carried out by using such a structure in which the buffer container 11 can be placed on the adapter AD lined with the rubber heater 12b.

While the rubber heater 12b can be arranged in contact with the buffer container 11, the term "contact" herein is not limited to an arrangement in which both the members are physically and direct in contact with each other, but both the members may be, for example, in indirect contact with each other. In other words, a sheet having a high heat conductance may be inserted between both the members. In essence, the term can mean that both the members are thermodynamically connected.

The temperature of the separation medium 4b in the plural sample injecting ends 3b can be controlled by using the temperature controlling part TCM1.

Temperature controlling part TCM1 allows the temperature of the buffer solution 11a to be regulated. The buffer solution 11a of the buffer container 11 can be accessed twice during a run. First, the buffer 11a can be used to enable pre-electrophoresis of the separation medium 4b. This step can help flush out ions that accumulate over time as the separation medium 4b ages. After pre-electrophoresis, the injecting end 3b can be washed in deionized water and moved to the sample for injection. After injection, the end 3b can be washed again before the final insertion in a buffer for the sample electrophoresis. To insure maximum denaturation the buffer can be heated. However, heating the buffer can cause problems according to various embodiments.

According to various embodiments, a heater, temperature sensor and thermal fuse are integrated in a holder for a buffer chamber. A rubber duckbill septa was placed over the chamber top to control evaporation while enabling insertion of the capillary ends. Software and firmware can be used to enable control and monitoring of the buffer chamber temperature. To provide sample denaturation, buffer can be heated above ambient. The actual temperature of the buffer can be programmable and can be application specific. Under some conditions, the transition from warm buffer to wash reagent or sample can result in a section of the capillary being cooled. The separation medium can shrink and draw in fluid from the open ends of the capillary (mainly the open end near the temperature transition). This can degrade the run performance.

According to various embodiments, this degradation can be corrected, for example, by pushing a small amount, for example, from about 0.05 μl to about 0.5 μl per cap of cooled and shrunk separation medium out of the end of the capillary during transfer of the capillary, for example, and then washing the polymer off the end. Because only a small amount is removed or displaced, to make up for shrinkage volume loss, the benefits of an electrophoretic prerun are not eliminated. According to various embodiments, the degradation can be corrected by changing the construction of the capillary array load end to eliminate any air gap between the metal electrode and the capillary, for example, such that the electrode surrounds and contacts the capillary.

These steps can allow various advantages to be achieved. For example, by heating the injection end of the capillary, the sizing accuracy is improved. Furthermore, by controlling the temperature over more of the capillary, the precision and run is more consistent between different runs in which the room temperature is changed. Moreover, the improved denaturation, due to heat, of the separation medium can enable the use of alternate separation medium which has a lower amount of denaturants added. These alternate formulations can run faster.

The temperature controlling part TCM2 controlling the temperature of the detector part 1 will be described with reference to FIGS. 4(a) to 5(c).

Figure 4C:
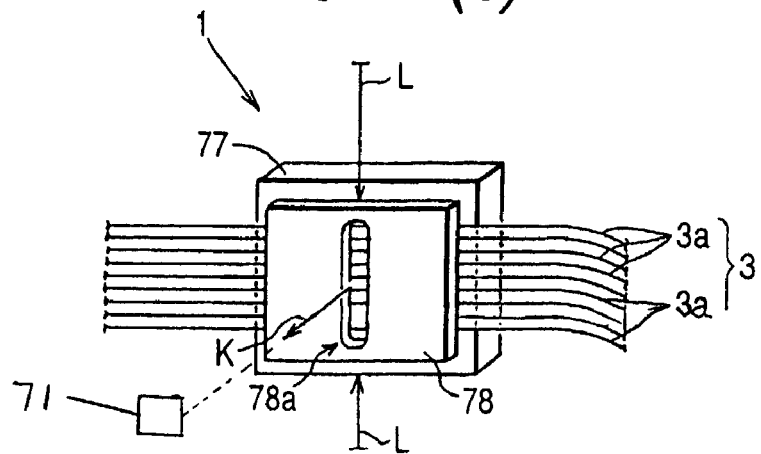

As shown in FIGS. 4(a) to 4(c), the multi-capillary 3 formed with plural capillaries 3a can be supported by clamping between a capillary supporting component 77 made with, for example, a glass plate, and a pressing member 78. An outer periphery of the capillaries 3a can be covered with a light shielding resin 51a, such as polyimide. A region that is not coated with the light shielding resin 51a can be provided on the outer periphery of the capillaries 3a between the capillary supporting part 77 and the pressing member 78.

According to various embodiments, the region can be irradiated with laser light L. This region is referred to as a detecting component 3c. An opening 78a can be formed in the region containing the detecting component 3c in the pressing member 78. Emission light K generated upon irradiating the sample with the laser light can be radiated to the exterior through the opening 78a. The structures described herein are totally referred to as a detector component.

According to various embodiments, fluctuation in intensity depending on the position of the laser light L incident on the capillaries 3a can be suppressed by irradiating the capillaries 3a with the laser light L from both above and beneath.

Figure 5A:
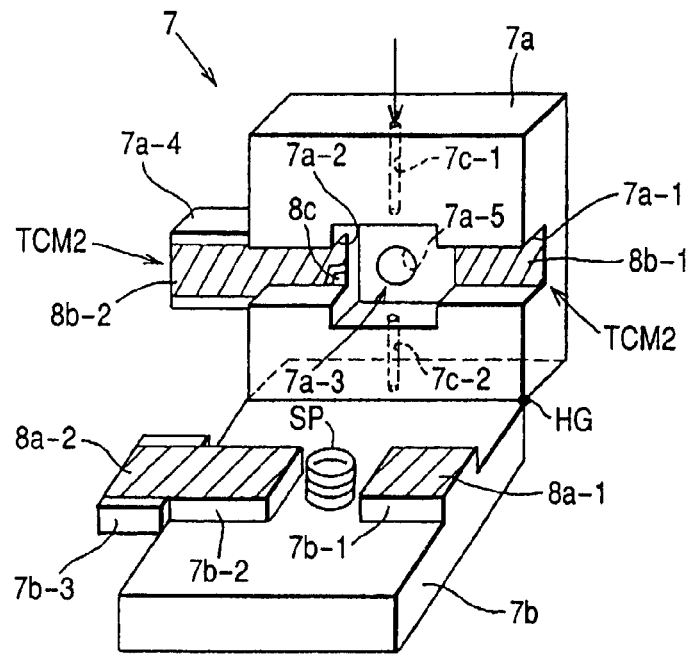
FIGS. 5(*a*) to 5(*c*) illustrate a structure of the container component that contains the detector component and the temperature controlling part controlling the temperature of the detector component in the multi-capillary electrophoresis apparatus according to various embodiments, and also illustrates the arrangement of the optical mechanism.
Figure 5B:
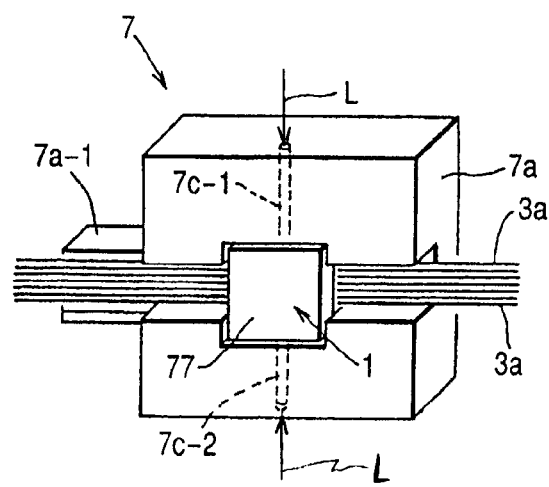
Figure 5C:
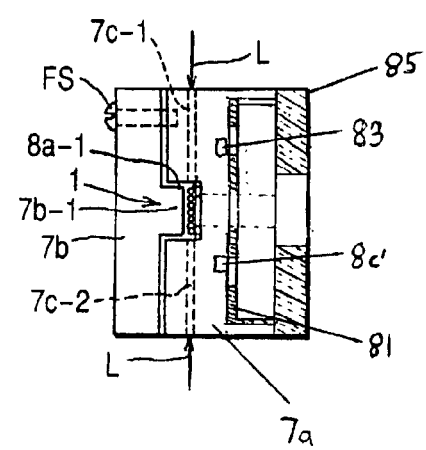

As shown in FIGS. 5(a) to 5(c), the capillary supporting component 77 and the pressing member 78, as well as the multi-capillary 3 supported therebetween, can be contained in a container component 7. The container component 7 can constitute a main body 7a and a cover member 7b. The main body 7a and the cover member 7b can be connected with a hinge HG as a central axis.

According to various embodiments, the main body 7a is made of a thermally conductive material (such as aluminum). It can have a container component 7a-3, which can contain the detector component 1, a groove 7a-1 and a groove 7a-2, which can be connected to the container component 7a-3 and extend toward both sides, and a protrusion component 7a-4, which can be connected to the groove 7a-2 and can protrude from the side surface of the main body. The groove 7a-1, the groove 7a-2 and the protrusion component 7a-4 have a flat plane, on which the multi-capillary 3 can be arranged. The container component 7a-3 forms a concave part that is deeper than the flat plane. An opening 7a-5 penetrating the main body 7a can be formed in the concave part and facilitates collection of fluorescent light.

In the cover member 7b a spring member SP can be provided at a position corresponding to the container component 7a-3. Upon closing the cover member 7b, and securing fixing screw FS, the spring member SP can press on the detector component 1, holding it securely. A convex part 7b-1 and a convex part 7b-2 engaging with the groove 7a-1 and the groove 7a-2, respectively, can be provided at positions corresponding to the grooves on both sides of the container part 7a-3. A protrusion component 7b-3 extending from the convex part 7b-2 can also be provided at a position corresponding to the protrusion component 7a-4. Thermally conductive rubber 8b-1 and 8b-2 along with complementary insulating rubber parts 8a-1 and 8a-2 press against the capillaries to provide good thermal contact with the main body 7a.

FIG. 5(b) shows a state in which the capillary supporting component 77 and the pressing member 78 (FIG. 4c) are contained in the container component 7a-3, and the multi-capillary array 3 is contained in the groove 7a-1 and the groove 7a-2. A through hole 7c-1, and a through hole 7c-2, can be formed whereby laser light L can reach a position corresponding to the detecting component 3c (FIG. 4(b)).

According to various embodiments, and referring to FIG. 5(c), the temperature controlling part TCM2 provided in the vicinity of the detector component 1 can contain, for example, at least one heater 81 and at least one temperature monitor 8c' and a thermal fuse 83 for safety. The heater 81 and temperature monitor 8c' and thermal fuse 83 can be mounted to the main body 7a. A thermal insulator 85 can be provided to reduce heat loss to the main optics casting (not shown).

Figure 6A:
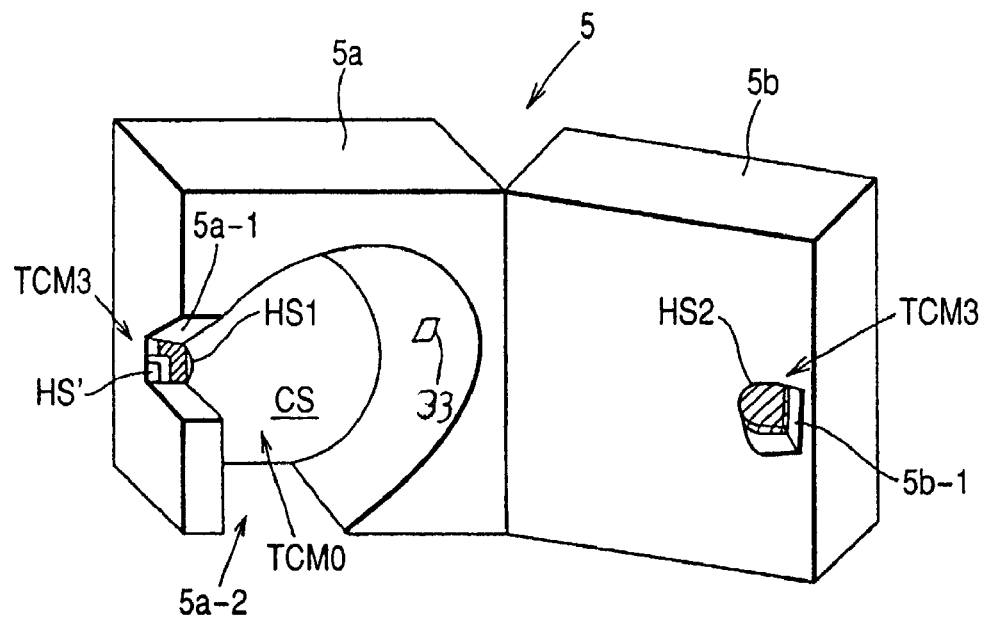
FIGS. 6(*a*) and 6(*b*) illustrate a structure of the temperature controlling part that controls the temperatures among the capillaries in the vicinity of the outlet of the temperature regulated chamber in the multi-capillary electrophoresis apparatus according to various embodiments.
Figure 6B:
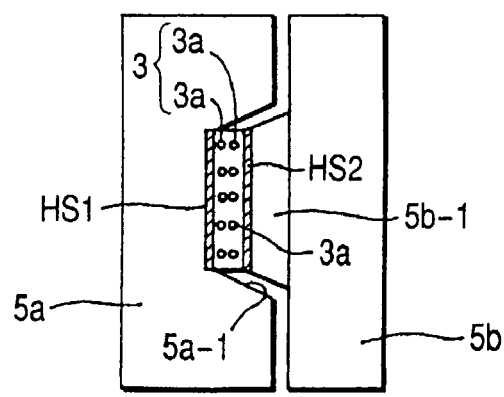

The temperature controlling part TCM3 will be described with reference to FIGS. 6(a) and 6(b). According to various embodiments, the multi-capillary array 3 in the capillary containing component CS in the temperature regulated chamber 5 can be connected to the detector component 1 through the temperature regulated chamber 5. An opening can be formed on a side of the detector component 1 in the vicinity of the temperature regulated chamber 5. A concave part 5a-1 can be formed on a main body 5a of the temperature regulated chamber 5, and a convex part 5b-1 engaging with the concave part 5a-1 can be formed on a cover component 5b of the temperature regulated chamber 5. The multi-capillary array 3 can be inserted in a gap formed between the concave part 5a-1 and the convex part 5b-1 formed upon closing the cover component 5b.

According to various embodiments, the temperature controlling part TCM3 can contain rubber heaters HS1 and HS2 attached to the surfaces of the concave part 5a-1 and the convex component 5b-1 facing each other, and a temperature monitor HS' can be provided in the vicinity thereof. The rubber heater can be attached to one of the facing surfaces of the concave component 5a-1 and the convex component 5b-1. A thermal conductor sheet can be attached instead of the rubber heater, or in alternative, both of them can be accumulated and attached.

The temperature of the separation medium among the capillaries of the multi-capillary array directed from the temperature regulated chamber 5 to the detector component 1 can be controlled by the temperature controlling part TCM3.

The fourth temperature controlling part TCM4 and TCM5 will be described with reference to FIG. 7.

According to various embodiments, an upper polymer block 34 is, for example, a block formed with an acrylic resin. A syringe 31, a polymer storage container 25 and a buffer container 15 can be connected to the upper polymer block 34. Flow paths 31a to 31e can be formed in the upper polymer block 34.

According to various embodiments, a fresh polymer 34c can be filled in the polymer storage container 25. The polymer storage container 25 can be connected to an end of the flow path 31b through a tube path 34b. A first valve (check valve) V1 can be provided between an end of the tube path 34b and the flow path 31b to allow only the flow of the polymer from the polymer storage container 25 toward the upper polymer block 34.

According to various embodiments, the syringe 31 and the upper polymer block 34 can be connected at a connecting part 31'. When a pin valve PV is closed, and a plunger of the syringe 31 is withdrawn for reducing pressure, the fresh polymer 34c in the polymer storage container 25 can be filled into the syringe 31 through the tube path 34b, the flow path 31b and the flow path 31a. When the pin valve PV is closed, and the plunger of the syringe 31 is pressed, the polymer filled in the syringe 31 can be injected into the capillaries 3a through the flow path 31a, the flow path 31c and the flow path 31d. The polymer functions as the separation medium 4b inside the capillaries 3a. The separation medium 4b after analysis can be discharged outside the capillaries 3a through the sample injecting end 3b of the capillaries by again charging the fresh polymer by the foregoing operation.

According to various embodiments, a tube path 15b can be provided between the flow path 31e in the upper polymer block 34 and a flow path 15e of a lower polymer block 15c to connect them. The lower polymer block 15c has a protrusion part 15c' protruding downward. The pin valve PV for opening and shutting an end opening 15d of the flow path 15e can be attached to the lower polymer block 15c. A tip end of the pin valve PV can reach the interior of the protrusion part 15c'. The separation medium 4b can be filled in the flow path 31e in the upper polymer block 34, the tube path 15b, and the flow path 15e in the lower polymer block 15c. A buffer solution 15a can be filled in a buffer container 15. Alternatively, separation medium 4b may be filled into the buffer container 15 instead of the buffer solution. The separation medium 4b and the buffer solution 15a can be in contact with each other at the end opening 15d of the flow path 15e.

Upon carrying out electrophoresis, the pin valve PV can be moved in the withdrawing direction (upward in the figure). A tip end 6b' of an electrode 6b can be grounded. Upon opening the pin valve PV, an electrification path can be formed between the electrode 6a and the electrode 6b through the a) buffer solution 11a (between the electrode 6a and the sample injecting end 3b of the capillaries), b) the separation medium 4b (filled in the sample injecting end 3b of the capillaries), c) the capillaries 3 through the end part 3d thereof, d) the flow path 31e in the upper polymer block 34, e) the tube path 15b and the flow path 15e in the lower polymer block 15c, and f) the buffer solution 15a (between the end opening 15d of the flow path 15e and the electrode 6b).

Therefore, when the pin valve PV is opened, and a voltage is applied between the electrode 6a and the electrode 6b with the direct current power supply 21 (FIG. 1), such a voltage can be applied between both the ends of the electrification path (to be precise, the voltage is applied to the buffer solutions positioned on both ends of the separation medium, which are filled in the electrification path). Consequently, an electric current can be created in the separation medium 4b filled in the capillaries 3a.

The pin valve PV is closed when the polymer is replaced in the capillaries 3a. At this time, the separation medium can be injected from the polymer storage container 25 to the capillaries 3a with the syringe 31.

According to various embodiments, as the temperature controlling part TCM4, a rubber heater 36 can be arranged on an outer surface of the tube path 15b and a temperature monitor 36b can be attached to the outer surface of the tube path 15b exposed from an opening formed on the rubber heater 36. Alternatively, it is possible to provide a rubber heater HT attached to an outer surface of the buffer container 15 and a temperature monitor HT' attached to an exposed surface of the buffer container 15 exposed from an opening formed on the rubber heater HT. Both of them may be provided. A heater can also be provided on an outer surface of the upper polymer block 34 or in the interior thereof.

According to various embodiments, the buffer solution 11a and the buffer solution 15a can be prepared with, for example, a sodium ion and TAPS (N-tris(hydroxymethyl)methyl-3-aminopropanesulfonic acid). The tube path can be similarly immersed in the buffer solution 15a.

According to various embodiments, the buffer solutions 11a and 15a can be filled in the buffer containers 11 and 15, respectively. The electrode 6a and the electrode 6b can be immersed in the buffer solution 11a and the buffer solution 15a, respectively. The buffer solutions 11a and 15a can connect electrically between electrodes and the separation medium in the capillary.

Figure 7:
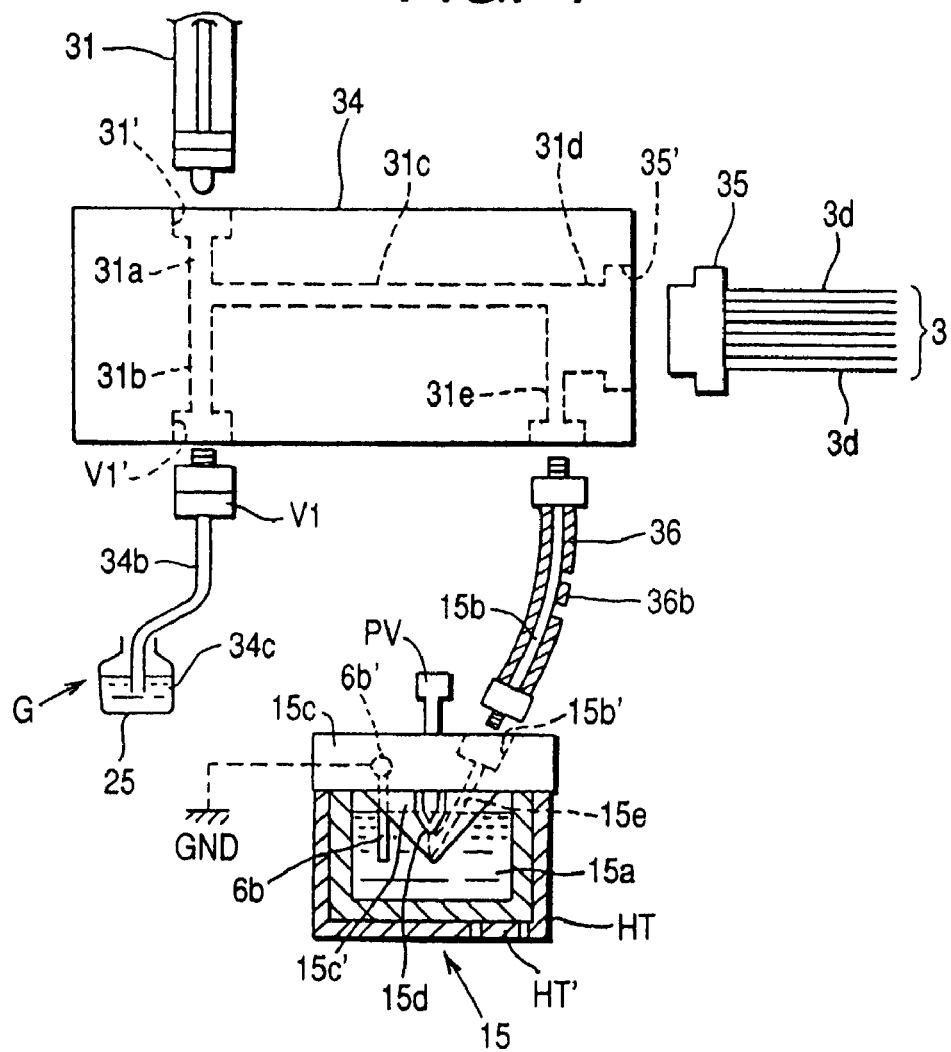
FIG. 7 illustrates the structures of the polymer block, the buffer container having the buffer solution filled therein, and the conduit connecting them in the multi-capillary electrophoresis apparatus according to various embodiments, and particularly illustrates the structure of the temperature controlling part that controls the temperature of the conduit and the buffer container.

In FIG. 7, an upper surface of the buffer solution 15a can be positioned above an end opening 15d of the flow path 15e. Therefore, at least a part of the protrusion part 15c' of the lower polymer block 15c can be immersed in the buffer solution 15a.

The temperature difference of the separation medium in the capillaries of the multi-capillary array in the vicinity of the buffer container can be suppressed by the temperature controlling part TCM4.

The temperature controlling part TCM5 will be described with reference to FIG. 1. According to various embodiments, the temperature controlling part TCM5 can control the temperature of at least one of the upper polymer block 34, the buffer solution 15a and the tube path 15b. According to various embodiments, the temperature controlling part TCM5 can be constituted with a temperature regulated region RH and a temperature monitor RH' equipped therein.

According to various embodiments, the temperature of the separation medium in the capillaries of the multi-capillary array in at least one region of the upper polymer block 34, the buffer solution 15a, and the tube path 15b can be controlled by the temperature controlling part TCM5.

Figure 8:
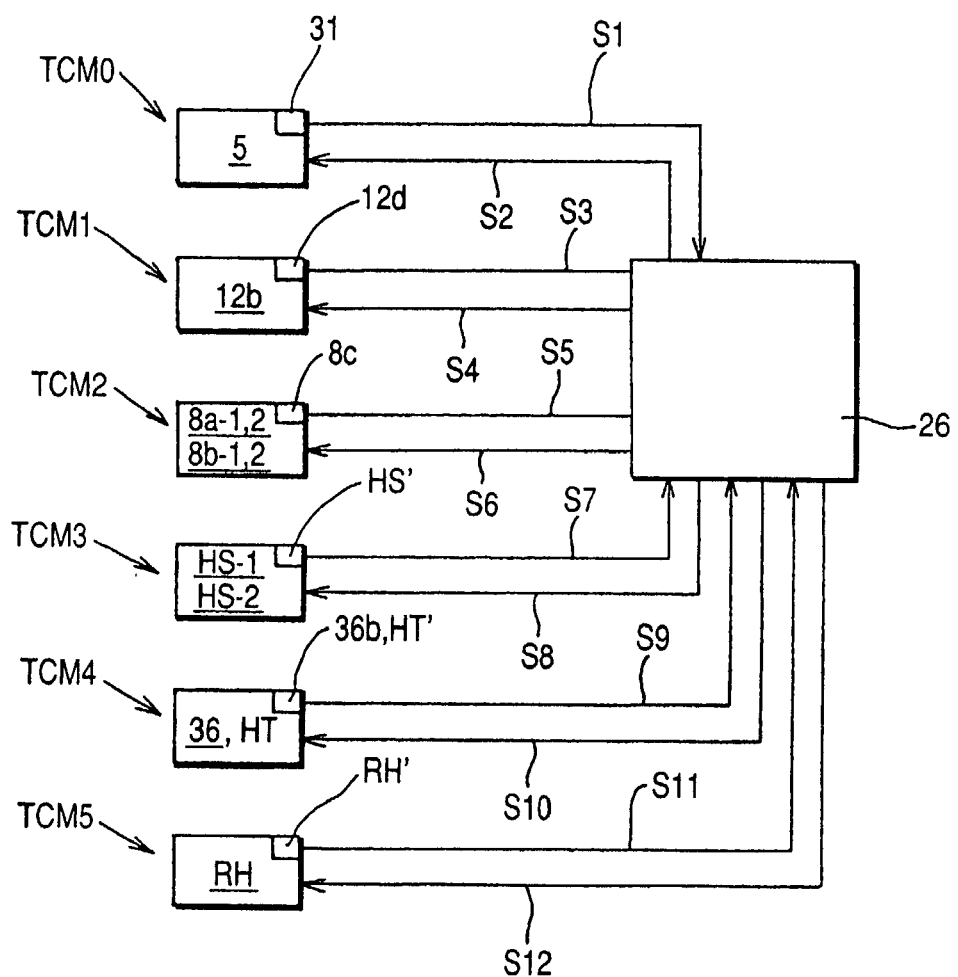
FIG. 8 illustrates the relationship between the controlling component and the respective temperature controlling parts in the multi-capillary electrophoresis apparatus according to various embodiments.

A temperature controlling function provided in the electrophoresis apparatus A will be described with reference to FIG. 8.

According to various embodiments, a temperature controlling component 26 can be provided for carrying out the entire temperature control, for example, PID control. The temperature controller 26 can carry out the entire temperature control of the capillary electrophoresis apparatus A.

As described in the foregoing, a temperature monitor 33 can be provided in the temperature regulated chamber 5 for monitoring the temperature inside the temperature regulated chamber 5. According to various embodiments, the temperature monitor 33 can send a signal S1 to the controller 26, and the controller 26 can send a control signal S2 controlling the temperature in the temperature regulated chamber 5 based on the signal S1, whereby the basic temperature controlling part TCM0 is constituted.

According to various embodiments, the temperature controlling part TCM1 can contain the rubber heater 12b and the temperature monitor 12d. The temperature monitor 12d can send a signal S3 to the controller 26, and the controller 26 can send a control signal S4 to control the temperature of the buffer solution 11a based on the signal S3 through the rubber heater 12b.

According to various embodiments, the temperature controlling part TCM2 can contain the rubber heaters 8a-1 and 8a-2, the rubber heaters 8b-1 and 8b-2, and the temperature monitor 8c. The temperature monitor 8c can send a signal S5 to the controller 26, and the controller 26 can send a control signal S6 to control the temperature of the separation medium 4b in the vicinity of the detector part 1 (in the detecting component 3c of the capillaries) based on the signal S5.

According to various embodiments, the temperature controlling part TCM3 can contain the rubber heaters HS1 and HS2 and the temperature monitor HS'. The temperature monitor HS' can send a signal S7 to the controller 26, and the controller 26 can send a control signal S8 to control the temperature in the vicinity of the outlet of the temperature regulated chamber 5 based on the signal S7 through the rubber heaters HS1 and HS2.

According to various embodiments, the temperature controlling part TCM4 can contain the heater 36 and the temperature monitor 36b, and further can contain the heater HT and the temperature monitor HT', which can be in contact with the outer peripheral surface of the buffer container 15. The temperature monitor 36b and the temperature monitor HT' can send a signal S9 to the controller 26, and the controller 26 can send a control signal S10 to control the temperature of the separation medium 4b in the vicinity of the upper polymer block 34 based on the signal S9 through the heaters 36 and HT.

According to various embodiments, the temperature controlling part TCM5 can contain the temperature regulated region RH and the temperature monitor RH' can be provided inside the temperature regulated region RH. The temperature monitor RH' can send a signal S11 to the controller 26, and the controller 26 can send a control signal S12 to control the temperature of the temperature regulated region RH based on the signal S11.

According to various embodiments, while the rubber heater 12b can be provided in contact with the bottom surface of the buffer container 11, it can be provided on the outer side surface of the buffer container 11. The rubber heater 12b can be provided on one of the bottom surface and the side surface, and can also be provided on both of them. Furthermore, the buffer container 11 can be placed on a heater to carry out the temperature control.

According to various embodiments, the temperature controller 26 can send the temperature control signals S2, S4, S6, S8, S10 and S12 to the temperature regulated chamber or the heaters based on the signals S1, S3, S5, S7, S9 and S11 sent from the temperature monitors to the controller 26, whereby the temperature control can be accomplished. As the temperature monitor, for example, a platinum resistance thermometer and a thermocouple can be used.

As a method for temperature control, for example, the PID (proportional integral derivation) control can be used as described in the foregoing. Such a method can be used such that the detection output from the temperature monitor can be subjected to feedback to the heater or Peltier element(s).

According to various embodiments, the temperature control can be carried out to reduce the difference of the temperatures in the radial direction of the plural capillaries 3a, for example, the temperatures of the separation medium in the respective capillaries at positions equidistant from the ends thereof. For example, when the temperature measured by the temperature monitor 33 attached to the temperature regulated chamber 5 and the temperatures of the other parts are controlled to reduce the difference therefrom, there is such a tendency that the temperature difference in the radial direction is reduced.

According to various embodiments, a method for using the multi-capillary electrophoresis apparatus A (i.e., a method for analyzing a sample) will be briefly described below.

According to various embodiments, the separation medium 4b can be filled in the capillaries 3a by using the syringe 31. For example, 16 capillaries 3a can be used. Subsequently, a sample 4a containing plural kinds of DNA molecules having different base lengths (DNA fragment sample) can be introduced to the separation medium 4b filled in the capillaries 3a through the sample injecting end 3b. The sample injecting end 3b can be immersed in the buffer solution 11a filled in the buffer container 11. The PID control can be carried out with the temperature controller 26 to reduce the temperature difference among the plural capillaries 3a.

The temperature control can be carried out to reduce the temperature difference in the radial direction of the plural capillaries 3a by using at least one of the temperature controlling parts. Under the continued temperature control, a high voltage, for example, about from 10 to 20 kV, can be applied between the electrode 6a (cathode) and the electrode 6b (anode) with the direct current power supply 21.

The DNA molecules migrate toward the electrode 6 (electrophoresed) because they are negatively charged. Differences in electrophoresis migration velocity of the DNA molecules occur corresponding to the base lengths thereof. The molecules having smaller base lengths exhibit larger electrophoresis migration velocities thereby requiring shorter periods of time to reach the detecting part 3c. Upon irradiating the sample (DNA molecules) reaching the detecting part 3c with laser light L, identification markers attached to the DNA molecules can be excited to cause fluorescence. The fluorescence is collected and imaged onto a photon sensing device (CCD image sensor) provided in a CCD camera 71. According to various embodiments, DNA molecules can be distinguished by electric signals obtained from the CCD camera 71, and thus the DNA can be analyzed. Consequently, a sample containing DNA fragments can be subjected to electrophoresis, and fluorescence from the sample can be detected in the course of electrophoresis, whereby the DNA base sequencing can be carried out for determining the base sequence.

According to various embodiments, the separation medium 4b and the sample 4a can be discharged to the outside through the injection end 3b According to various embodiments, the separation medium 4b can be replaced per analysis of one sample, and a fresh separation medium 4b can be used for analysis of a new sample.

Figure 9:
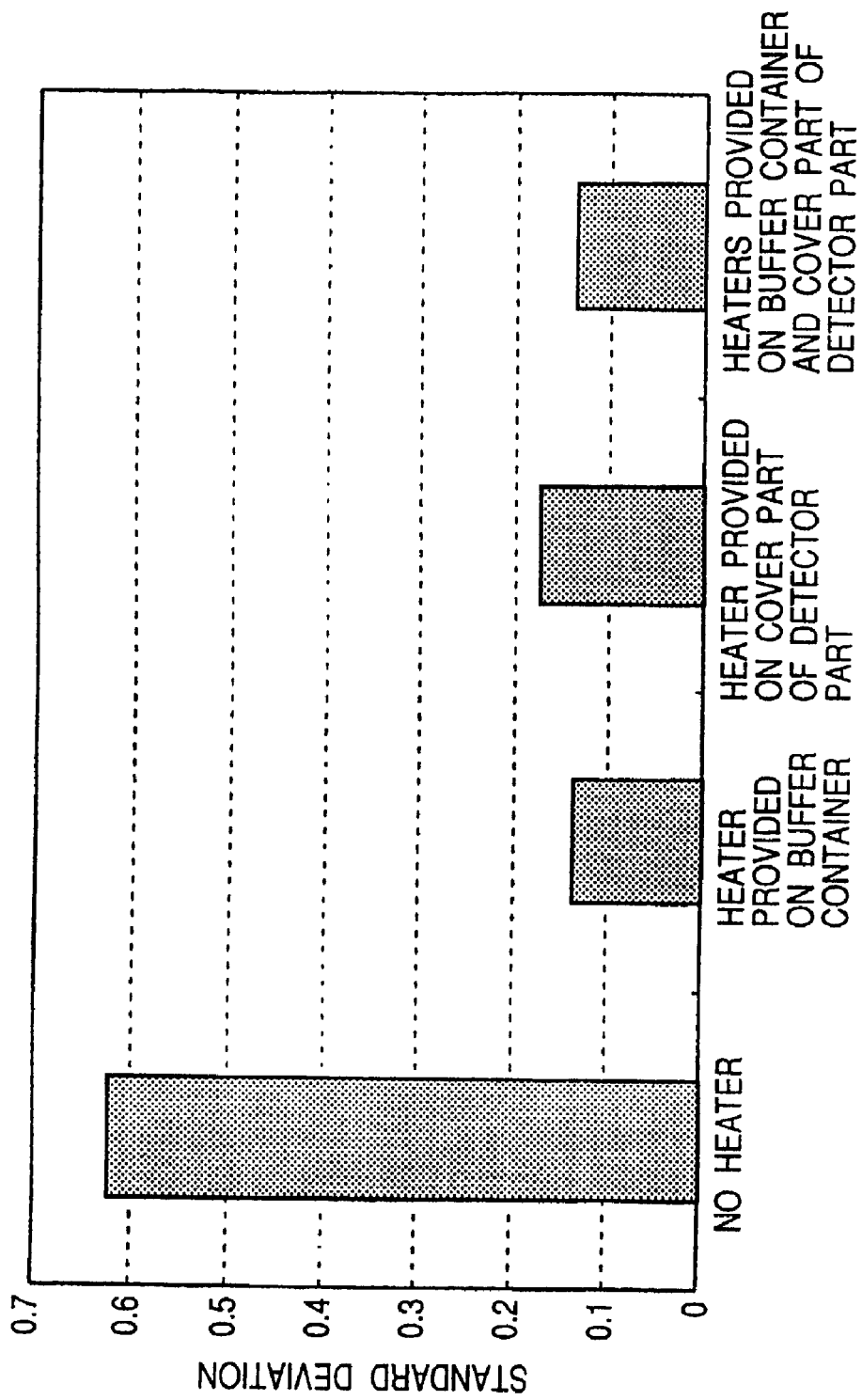
FIG. 9 is a graph showing a standard deviation of the electrophoresis time among the capillaries upon using the multi-capillary electrophoresis apparatus according to various embodiments.

FIG. 9 shows standard deviations of electrophoresis time in the case where 16 capillaries 3a are used, in which a sample is injected, and the capillaries are simultaneously subjected to electrophoresis under the same conditions. The data shown in FIG. 9 are experimental results in the case where the temperature controlling part TCM1 and the temperature controlling part TCM2 are attached to the buffer container 11 and the detector part 1, respectively.

According to various embodiments, when no temperature controlling part is provided on the buffer container 11 and the detector component 1 (i.e., an ordinary electrophoresis apparatus), the standard deviation of electrophoresis time among the 16 capillaries 3a is about 0.62. On the other hand, in the case where only the temperature controlling part TCM1 is provided, the standard deviation of electrophoresis time of the 16 capillaries 3a is about 0.16. In the case where only the temperature controlling part TCM2 is provided, the standard deviation of electrophoresis time of the 16 capillaries 3a is about 0.13.

In the case where both the temperature controlling part TCM1 and the temperature controlling part TCM2 are provided, the standard deviation of electrophoresis time of the 16 capillaries 3a is about 0.13.

It can be understood from the results that the difference of the electrophoresis time among the 16 capillaries can be reduced by providing a temperature controlling part on one of the buffer container 11 and the detector part 1 for carrying out temperature control.

According to the multi-capillary electrophoresis apparatus of the various embodiments, fluctuation of the electrophoresis migration velocity in the radial direction of plural capillaries can be suppressed.

Therefore, the analysis of a sample can be carried out in a more accurate manner by using the multi-capillary electrophoresis apparatus of the various embodiments While the invention describes a multi-capillary electrophoresis instrument it is understood that the ideas extend to a single capillary system or other electrophoresis approaches such as channel plates.

Those skilled in the art can appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed is:

1. A multi-capillary electrophoresis apparatus comprising:
   a multi-capillary array having a plurality of capillaries filled with an isolation medium for isolating a sample, a sample injecting end on one end thereof and a detector part for acquiring information depending on the sample at a position remote from the sample injecting end, the detector part being enclosed in a container;
   a voltage applying part for applying a voltage to an electrification path between the sample injecting end and the detector part;
   a thermostat oven containing the multi-capillary array except for portions that protrude from the thermostat oven, wherein the thermostat oven has a first temperature controlling part for controlling a temperature of the thermostat oven;
   a flow path, filled with the isolation medium and connected to the multi-capillary array;
   a second temperature controlling part for controlling a temperature of a portion of the multi-capillary array located between the detector part and the thermostat oven; and
   a third temperature controlling part capable of controlling a temperature of the multi-capillary array located beyond the detector part;
   wherein the first temperature controlling part is capable of controlling a temperature of the thermostat oven, separately from the temperature of the multi-capillary array located beyond the detector part and controlled by the third temperature controlling part.

2. A multi-capillary electrophoresis apparatus comprising:
   a multi-capillary array adapted to be filled with a separation medium for isolating a sample, comprising a first sample injecting end at one end, and a second end;
   a detector component for acquiring information from a sample in the multi-capillary array at a position remote from the sample injecting end;
   a voltage applying component for applying a voltage to an electrification path comprising the sample injecting end and the detector component, the voltage driving the sample in a direction of electrophoretic flow along the electrification path from the sample injecting end to the second end;
   a temperature regulated chamber containing substantially all of the multi-capillary array except for the first sample injecting end and the second end;
   a buffer container disposed outside the temperature regulated chamber and adapted to contain a buffer solution into which the sample injecting end, from which ends of capillaries protrude, is adapted to be immersed;
   a first temperature controlling part for controlling a temperature of the temperature regulated chamber;
   a second temperature controlling part capable of controlling a temperature of the buffer solution in the buffer container, separately from the temperature of the temperature regulated chamber;
   a third temperature controlling part for controlling a temperature of the detector component;
   a fourth temperature controlling part for controlling a temperature of a portion of the multi-capillary array between the temperature regulated chamber and the detector component; and
   a fifth temperature controlling part capable of controlling a temperature of the multi-capillary array located beyond the detector component:
   wherein the first temperature controlling part is capable of controlling the temperature of the temperature regulated chamber separately from the temperature of the multi-capillary array located beyond the detector component controlled by the fifth temperature controlling part, and the temperature controlling parts are arranged along the electrification path in the direction of the electrophoretic flow beginning wit the second temperature controlling part, followed by the first temperature controlling part, followed by the fourth temperature controlling part, followed by the third temperature controlling part.

3. The multi-capillary electrophoresis apparatus of claim 2, wherein the second temperature controlling part comprises a heater in contact with the buffer container.

4. The multi-capillary electrophoresis apparatus of claim 2, wherein the detector component comprises a photon accepting unit capable of receiving emission light generated upon irradiating the sample with excitation light.

5. The multi-capillary electrophoresis apparatus of claim 2, further comprising additional temperature controlling parts capable of heating portions of the apparatus to temperatures different from a temperature of the temperature regulated chamber.

6. The multi-capillary electrophoresis apparatus of claim 2, wherein the voltage applying component surrounds the sample injecting end of each capillary of the multi-capillary array and the apparatus is free of an air gap between the capillaries and the voltage applying component.

7. A multi-capillary electrophoresis apparatus comprising:
   a multi-capillary army adapted to be filled with a separation medium for isolating a sample, comprising a first sample injecting end at one end thereof, and a second end;
   a detector component for acquiring information from a sample in the multi-capillary array at a position remote from the sample injecting end and between the sample injecting end and the second end;

a voltage applying component for applying a voltage to an electrification path comprising the sample injecting end and the detector component, the voltage driving the sample in a direction of electrophoretic flow along the electrification path from the sample injecting end to the second end;

a temperature regulated chamber containing substantially all of the multi-capillary array except for at least a portion of the multi-capillary array in a vicinity of the detector component;

a buffer container disposed outside the temperature regulated chamber and adapted to contain a buffer solution into which the sample injecting end, from which ends of capillaries protrude, is adapted to be immersed;

a first temperature controlling part capable of controlling a temperature of the multi-capillary array between the temperature regulated chamber and the detector component;

a separate second temperature controlling part capable of controlling a temperature of the multi-capillary array located beyond the detector component;

a third temperature controlling part for controlling a temperature of the detector component; and a fourth temperature controlling part for controlling a temperature of the temperature regulated chamber, separately from the temperature of the multi-capillary array located beyond the detector component controlled by the second temperature controlling part;

wherein the detector component is disposed outside the temperature regulated chamber and wherein the temperature controlling parts are arranged along the electrification path in the direction of the electrophoretic flow beginning with the fourth temperature controlling part, followed by the first temperature controlling part, followed by the third temperature controlling part, followed by the second temperature controlling part.

8. The multi-capillary electrophoresis apparatus of claim 7, wherein the first temperature controlling part comprises a heater arranged in a vicinity of the detector component.

9. The multi-capillary electrophoresis apparatus of claim 7, further comprising additional temperature controlling parts capable of heating portions of the apparatus to temperatures different from a temperature of the temperature regulated chamber.

10. A multi-capillary electrophoresis apparatus comprising:
a multi-capillary array adapted to be filled with a separation medium for isolating a sample, comprising a sample injecting end at one end thereof, and a second end;
a detector component for acquiring information from a sample in the multi-capillary array at a position remote from the sample injecting end;
a voltage applying component for applying a voltage to an electrification path comprising the sample injecting end and the detector component, the voltage driving the sample in a direction of electrophoretic flow along the electrification pat from the sample injecting end to the second end;
a temperature regulated chamber containing substantially all the multi-capillary array except for at least the sample injecting end and a portion of the multi-capillary array in the vicinity of the detector component;
a buffer container disposed outside the temperature regulated chamber and adapted to contain a buffer solution into which the sample injecting end, from which ends of capillaries protrude, is adapted to be immersed;
a first temperature controlling part capable of controlling a temperature of the buffer solution in the buffer container;
a second temperature controlling part capable of controlling a temperature of the detector component;
a third temperature controlling part for controlling a temperature of the temperature regulated chamber;
a fourth temperature controlling part for controlling a temperature of a portion of the multi-capillary array between the temperature regulated chamber and the detector component, wherein said first, second, third, and fourth temperature controlling parts are controllable separately from each other; and
a separate fifth temperature controlling part capable of controlling a temperature of the multi-capillary and located beyond the detector component:
wherein the temperature controlling parts are arranged along the electrification path in the direction of the electrophoretic flow beginning with the first temperature controlling part, followed by the third temperature controlling part, followed by the fourth temperature controlling part, followed by the second temperature controlling part.

11. The multi-capillary electrophoresis apparatus of claim 10, wherein the first temperature controlling part comprises a first heater for heating the buffer solution and a first sensor for measuring a temperature of the buffer solution, and the second temperature controlling part comprises a heater for heating the detector component and a second sensor for measuring a temperature of the detector component.

12. The multi-capillary electrophoresis apparatus of claim 10, further comprising additional temperature controlling pats capable of heating portions of the apparatus to temperatures different from a temperature of the temperature regulated chamber.

13. A multi-capillary electrophoresis apparatus comprising:
a multi-capillary array adapted to be filled with a separation medium for isolating a sample, comprising a sample injecting end at one end thereof, and a second end;
a detector component for acquiring information from a sample in the multi-capillary array at a position remote from the sample injecting end;
a voltage applying component for applying a voltage to an electrification path comprising the sample injecting end and the detector component, the voltage driving the sample in a direction of electrophoretic flow along the electrification path from the sample injecting end to the second end;
a temperature regulated chamber containing substantially all of the multi-capillary array;
a buffer container disposed outside the temperature regulated chamber and adapted to contain a buffer solution into which the sample injecting end, from which ends of capillaries protrude, is adapted to be immersed;
a polymer block arranged outside the temperature regulated chamber for changing the separation medium in the capillary array; and
a first temperature controlling part capable of controlling a temperature of the polymer block, separately from the temperature of the temperature regulated chamber;
a second temperature controlling part for controlling a temperature of the temperature regulated chamber separately of the first temperature controlling part;

a third temperature controlling part for controlling a temperature of the detector component;

a fourth temperature controlling part for controlling a temperature of a portion of the multi-capillary array between the temperature regulated chamber and the detector component; and a fifth temperature controlling part capable of controlling a temperature of the multi-capillary array located beyond the detector component:

wherein the second temperature controlling part is capable of controlling a temperature of the temperature regulated chamber, separately from the temperature of the multi-capillary array located beyond the detector component and controlled by the fifth temperature controlling part, and the temperature controlling parts are arranged along the electrification path in the direction of the electrophoretic flow beginning with the second temperature controlling part, followed by the fourth temperature controlling part, followed by the third temperature controlling part, followed by the first temperature controlling part.

14. The multi-capillary electrophoresis apparatus of claim 13, further comprising additional temperature controlling parts capable of heating portions of the apparatus to temperatures different from a temperature of the temperature regulated chamber.

15. A multi-capillary electrophoresis apparatus comprising:

a multi-capillary array having a separation medium filled therein for isolating a sample, and comprising a sample injecting end at one end thereof;

a detector component for acquiring information from the sample in the multi-capillary array at a position remote from the sample injecting end;

a voltage applying component for applying a voltage to an electrification path comprising the sample injecting end and the detector component;

a temperature regulated chamber containing substantially all of the multi-capillary array;

a buffer container disposed outside the temperature regulated chamber and adapted to contain a buffer solution into which the sample injecting end, from which ends of capillaries protrude is adapted to be immersed;

a flow path connected to each of the capillaries of the multi-capillary array and situated beyond the detector component and having the separation medium filled therein; and a separate first temperature controlling part capable of controlling a temperature of the flow path;

a second temperature controlling part for controlling a temperature of the temperature regulated chamber, separately from at least a temperature of the buffer container;

a third temperature controlling part for controlling a temperature of the detector component;

a fourth temperature controlling part for controlling a temperature of a portion of the multi-capillary array between the temperature regulated chamber and the detector component; and a fifth temperature controlling part capable of controlling a temperature of the multi-capillary array located beyond the detector component;

wherein the second temperature controlling part is capable of controlling a temperature of the temperature regulated chamber, separately from the temperature of the multi-capillary array located beyond the detector component and controlled by the fifth temperature controlling part.

16. The multi-capillary electrophoresis apparatus of claim 15, further comprising additional temperature controlling parts capable of heating portions of the apparatus to temperatures different from a temperature of the temperature regulated chamber.

17. A multi-capillary electrophoresis apparatus comprising:

a multi-capillary array having a separation medium filled therein for isolating a sample, and comprising a sample injecting end, from which ends of capillaries protrude, at one end thereof, and a second end;

a detector component for acquiring information from the sample in the multi-capillary array at a position remote from the sample injecting end;

a voltage applying component for applying a voltage to an electrification path comprising the sample injecting end and the detector component, the voltage driving the sample in a direction of electrophoretic flow along the electrification path from the sample injecting end to the second end;

a temperature regulated chamber containing substantially all of the multi-capillary array;

a flow path connected to each of the capillaries of the multi-capillary array and having the separation medium filled therein;

a buffer container disposed outside the temperature regulated chamber and containing a buffer solution into which the flow path is immersed; and a first temperature controlling part capable of controlling a temperature of the buffer solution in the buffer container, separately from the temperature of the temperature regulated chamber;

a second temperature controlling part for controlling a temperature of the temperature regulated chamber;

a third temperature controlling part for controlling a temperature of the detector component;

a fourth temperature controlling part for controlling a temperature of a portion of the multi-capillary array between the temperature regulated chamber and the detector component; and a fifth temperature controlling part capable of controlling a temperature of the multi-capillary array located beyond the detector component;

wherein the second temperature controlling part is capable of controlling a temperature of the temperature regulated chamber, separately from the temperature of the multi-capillary array located beyond the detector component and controlled byte fifth temperature controlling part, and the temperature controlling parts are arranged along the electrification path in the direction of the electrophoretic flow beginning with the first temperature controlling part, followed by the second temperature controlling part, followed by the fourth temperature controlling part, followed by the third temperature controlling part 18. The multi-capillary electrophoresis apparatus of claim 17, wherein the first temperature controlling part comprises a heater in contact with the buffer container.

19. The multi-capillary electrophoresis apparatus of claim 17, wherein the detector component comprises a photon accepting unit capable of receiving emission light generated upon irradiating the sample with excitation light.

20. The multi-capillary electrophoresis apparatus of claim 17, further comprising additional temperature controlling parts capable of heating portions of the apparatus to temperatures different from a temperature of the temperature regulated chamber.

21. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end;
- a thermostat oven containing all or a part of the multi-capillary array except for the sample injecting end;
- a buffer container, disposed outside the thermostat oven, containing a buffer solution in which the sample injecting end, from which ends of capillaries protrude, is immersed;
- a first temperature controlling part for controlling a temperature of the thermostat oven;
- a second temperature controlling part for controlling a temperature of the buffer solution in the buffer container, separately from the first temperature controlling part of the thermostat oven;
- a third temperature controlling part for controlling a temperature of the detector part, separately from the first and second temperature controlling parts;
- a fourth temperature controlling part for controlling a temperature of a vicinity of an outlet of the thermostat oven located to a side of the detector part, separately from the first, second, and third temperature controlling parts; and
- a fifth temperature controlling part capable of controlling a temperature of the multi-capillary array located beyond the detector part;
- wherein the first temperature controlling part is capable of controlling a temperature of the thermostat oven, separately from the temperature of the multi-capillary array located beyond the detector part and controlled by the fifth temperature controlling part, and the temperature controlling parts are arranged along a path in a direction from the sample injecting part to the detector part beginning with the second temperature controlling part, followed by the first temperature controlling part, followed by the fourth temperature controlling part, followed by the third temperature controlling part.

22. A multi-capillary electrophoresis apparatus as claimed in claim 21, wherein the detector part comprises a photo accepting unit receiving excitation light generated upon irradiating the sample with laser light, and a Peltier element for cooling the photo acceptance unit or heating the detector part.

23. A multi-capillary electrophoresis apparatus as claimed in claim 21, wherein the second temperature controlling part comprises a heater in contact with the buffer container.

24. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end;
- a thermostat oven containing all or a part of the multi-capillary array except for the detector part, wherein the detector part is disposed outside the thermostat oven;
- a buffer container, disposed outside the thermostat oven, containing a buffer solution in which the sample injecting end, from which ends of capillaries protrude, is immersed;
- a first temperature controlling part for controlling a temperature of the thermostat oven and the buffer solution;
- a second temperature controlling part for controlling a temperature of the detector part, separately from the thermostat oven and the buffer solution,
- a third temperature controlling part for controlling a temperature of a vicinity of an outlet of the thermostat oven located to a side of the detector part, separately from the thermostat oven, the buffer solution and the detector part; and
- a fourth temperature controlling part capable of controlling a temperature of the multi-capillary array located beyond the detector part;
- wherein the first temperature controlling part is capable of controlling a temperature of the thermostat oven, separately from the temperature of the multi-capillary array located beyond the detector part and controlled by the fourth temperature controlling part, and the temperature controlling parts are arranged along a path in a direction from the sample injecting part to the detector part beginning with the first temperature controlling part, followed by the third temperature controlling part, followed by the second temperature controlling part.

25. A multi-capillary electrophoresis apparatus as claimed in claim 24, wherein the second temperature controlling part comprises a heater arranged in a vicinity of the detector part.

26. A multi-capillary electrophoresis apparatus comprising
- a multi-capillary array having an isolation medium filled therein for isolating a sample, a sample injecting end on one end thereof, and a detector part for acquiring information depending on the sample at a position remote from the sample injecting end;
- thermostat oven containing all or a part of the multi-capillary array except for the sample injecting end and the detector part, the thermostat oven being adjacent and to a side of the detector part;
- a buffer container, disposed outside the thermostat oven, containing a buffer solution in which the sample injecting end, from which ends of capillaries protrude, is immersed;
- a first temperature controlling part for controlling a temperature of the buffer solution;
- a second temperature controlling part for controlling a temperature of the detector part;
- a third temperature controlling part for controlling a temperature of the thermostat oven;
- a fourth temperature controlling part for controlling a temperature in the vicinity of the detector part, in between the thermostat oven and the detector part, wherein said first, second, third, and fourth temperature controlling parts control separately from each others; and
- a fifth temperature controlling part capable of controlling a temperature of the multi-capillary array located beyond the detector part;
- wherein the third temperature controlling part is capable of controlling a temperature of the thermostat oven, separately from the temperature of the multi-capillary array located beyond the detector part and controlled by the fifth temperature controlling part, and the temperature controlling parts are arranged along a path in a direction from the sample injecting part to the detector part beginning with the first temperature controlling part, followed by the third temperature controlling part, followed by the fourth temperature controlling part, followed by the second temperature controlling part.

27. A multi-capillary electrophoresis apparatus as claimed in claim 26, wherein the first temperature controlling part comprises a first heater for heating the buffer solution and a first sensor for measuring a temperature of the buffer solution; and the second temperature controlling part comprises a heater for heating the detector part and a second sensor for measuring a temperature of the detector part.

28. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end;
- a thermostat oven containing all or a part of the multi-capillary array except for the detector part;
- a buffer container, disposed outside the thermostat oven, containing a buffer solution in which the sample injecting end, from which ends of capillaries protrude, is immersed;
- a first temperature controlling part for controlling a temperature of the thermostat oven;
- a second temperature controlling part for controlling a temperature of the buffer solution;
- a third temperature controlling part for controlling a temperature of the detector part;
- a fourth temperature controlling part for controlling a temperature in a vicinity of an outlet of the thermostat oven on a side of the detector part, wherein the temperatures of the thermostat oven, the buffer solution, and the detector part are separately controlled; and
- a fifth temperature controlling part capable of controlling a temperature of the multi-capillary array located beyond the detector part;
- wherein the first temperature controlling part is capable of controlling a temperature of the thermostat oven, separately from the temperature of the multi-capillary array located beyond the detector part and controlled by the fifth temperature controlling part, and the temperature controlling parts are arranged along a path in a direction from the sample injecting part to the detector part beginning with the second temperature controlling part, followed by the first temperature controlling part, followed by the fourth temperature controlling part, followed by the third temperature controlling part.

29. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end, the detector part being enclosed in a container;
- a thermostat oven containing all or a part of the multi-capillary array;
- a buffer container, disposed outside the thermostat oven, containing a buffer solution in which the sample injecting end, from which ends of capillaries protrude, is immersed;
- a gel block arranged outside the thermostat oven and charging the isolation medium in the capillary array, the gel block being operably connected by a first connection to the multi-capillary array and by a second connection to an isolation medium container, for filling the capillaries of the multi-capillary array with isolation medium from the isolation medium container;
- a first temperature controlling part for controlling a temperature of the thermostat oven and the buffer solution;
- a second temperature controlling part for controlling a temperature of the detector part;
- a third temperature controlling part for controlling a temperature of the gel block, separately from the temperatures of the thermostat oven, the buffer solution, and the detector part;
- a fourth temperature controlling part capable of controlling a temperature of the multi-capillary array located beyond the detector part; and
- a fifth temperature controlling part for controlling a temperature in a vicinity of an outlet of the thermostat oven on a side of the detector part;
- wherein the first temperature controlling part is capable of controlling a temperature of the thermostat oven, separately from the temperature of the multi-capillary array located beyond the detector part and controlled by the fourth temperature controlling part, and the temperature controlling parts are arranged along a path in a direction from the sample injecting part to the detector part beginning with the first temperature controlling part, followed by the second temperature controlling part, followed by the third temperature controlling part.

30. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end;
- a thermostat oven containing all or a part of the multi-capillary array;
- a buffer container, disposed outside the thermostat oven, containing a buffer solution in which the sample injecting end, from which ends of capillaries protrude, is immersed;
- a first temperature controlling part for controlling a temperature of the thermostat oven;
- a second temperature controlling part for controlling a temperature of the buffer solution;
- a third temperature controlling part for controlling a temperature of the detector part,
- a fourth temperature controlling part for controlling a temperature of a vicinity of an outlet of the thermostat oven located to a side of the detector part;
- a fifth temperature controlling part for controlling a temperature of the flow path, wherein the temperatures of the thermostat oven, the buffer solution, the detector part, the vicinity of the outlet, and the flow path are separately controlled; and
- a sixth temperature controlling part capable of controlling a temperature of the multi-capillary array located beyond the detector part;
- wherein the first temperature controlling part is capable of controlling a temperature of the thermostat oven, separately from the temperature of the multi-capillary array located beyond the detector part and controlled by the sixth temperature controlling part, and the temperature controlling parts are arranged along a path in a direction from the sample injecting part to the detector beginning with the second temperature controlling part, followed by the first temperature controlling part, followed by the fourth temperature controlling part, followed by the third temperature controlling part, followed by the fifth temperature controlling part.

31. A multi-capillary electrophoresis apparatus comprising:
- a multi-capillary array having an isolation medium filled therein for isolating a sample, a sample injecting end on one end thereof, and a detector part for acquiring information depending on the sample at a position remote from the sample injecting end;
- a thermostat oven containing all or a part of the multi-capillary array;
- a flow path connected to each of the capillaries of the multi-capillary array and having the isolation medium filled therein;
- a buffer container, disposed outside the thermostat oven, containing a buffer solution in which the sample injecting end, from which ends of capillaries protrude, is immersed;
- a first temperature controlling part for controlling a temperature of the thermostat oven;
- a second temperature controlling part for controlling a temperature of the buffer solution;
- a third temperature controlling part for controlling a temperature of the detector part;
- a fourth temperature controlling part for controlling a temperature of a vicinity of an outlet of the thermostat oven located to a side of the detector part;
- a fifth temperature controlling part for controlling a temperature of the flow path, wherein the temperatures of the thermostat oven, the buffer solution, the detector part, the vicinity of the outlet, and flow path are separately controlled; and
- a sixth temperature controlling part capable of controlling a temperature of the multi-capillary array located beyond the detector part;
- wherein the first temperature controlling part is capable of controlling a temperature of the thermostat oven, separately from the temperature of the multi-capillary array located beyond the detector part and controlled by the sixth temperature controlling part.

32. A multi-capillary electrophoresis apparatus as claimed in claim 31, wherein the second temperature controlling part comprises a heater in contact with the buffer container.

33. A multi-capillary electrophoresis apparatus comprising:
- a multi-capillary array having a plurality of capillaries filled with an isolation medium for isolating a sample, a sample injecting end on one end thereof and a detector part for acquiring information depending on the isolated sample at a position remote from the sample injection end;
- a voltage applying part for applying a voltage to an electrification path between the sample injecting end and the detector part, the voltage driving the sample in a direction of electrophoretic flow along the electrification path from the sample injecting end to a second end opposite the sample injecting end;
- a thermostat oven containing the multi-capillary array except for portions of the multi-capillary array that protrude from the thermostat oven;
- a buffer container, disposed outside the thermostat oven, containing a buffer solution in which the sample injecting end, from which ends of capillaries protrude, is immersed;
- a first temperature controlling part for controlling a temperature of the thermostat oven and the buffer solution;
- second temperature controlling part that controls a temperature of the detector part separately from the temperatures of the thermostat oven and the buffer solution controlled by the first temperature controlling part;
- a third temperature controlling part for controlling a temperature of the multi-capillary array located beyond the detector part; and
- a fourth temperature controlling part for controlling a temperature in a vicinity of an outlet of the thermostat oven on a side of the detector part;
- wherein the first temperature controlling part is capable of controlling a temperature of the thermostat oven, separately from the temperature of the multi-capillary array located beyond the detector part and controlled by the third temperature controlling part, and the temperature controlling parts are arranged along the electrification path in the direction of the electrophoretic flow beginning with the first temperature controlling part, followed by the second temperature controlling part, followed by the third temperature controlling part.

34. A multi-capillary array electrophoresis apparatus comprising:
- a multi-capillary array having a plurality of capillaries filled with an isolation medium for isolating a sample injection end on one end thereof, and a detector part for acquiring information depending on the sample at a position remote from the sample injection end;
- a voltage applying part for applying a voltage to an electrification path between the sample injecting end and the detector part, the voltage driving the sample in a direction of electrophoretic flow along the electrification path from the sample injecting end to a second end opposite the sample injection end;
- a thermostat oven containing the multi-capillary array except for portions of the multi-capillary array that protrude from the thermostat oven, wherein the thermostat oven has a first temperature controlling part for controlling a temperature of the thermostat oven;
- a buffer container, disposed outside the thermostat oven, containing a buffer solution in which the sample injecting end, from which ends of capillaries protrude, is immersed;
- a second temperature controlling part that controls a temperature of the detector part separately from the temperatures of the thermostat oven, the buffer solution, and the detector part;
- a third temperature controlling part for controlling a temperature of the multi-capillary array located beyond the detector part; and
- a fourth temperature controlling part for controlling a temperature in a vicinity of an outlet of the thermostat oven on a side of the detector part;
- wherein the first temperature controlling part is capable of controlling a temperature of the thermostat oven, separately from the temperature of the multi-capillary array located beyond the detector part and controlled by the third temperature controlling part, and the temperature controlling parts are arranged along the electrification path in the direction of the electrophoretic flow beginning with the first temperature controlling part, followed by the second temperature controlling part, followed by the third temperature controlling part.

35. A multi-capillary electrophoresis apparatus comprising:
- a multi-capillary array having a plurality of capillaries filled with an isolation medium for isolating a sample, a sample injecting end on one end thereof and a detector part for acquiring information depending on the isolated sample at a position remote from the sample injection end;

a voltage applying part for applying a voltage to an electrification path between the sample injecting end and the detector part, the voltage driving the sample in a direction of electrophoretic flow along the electrification path from the sample injecting end to a second end opposite the sample injecting end;

a thermostat oven containing the multi-capillary array except for portions of the multi-capillary array that protrude from the thermostat oven, wherein the thermostat oven has a first temperature controlling part for controlling a temperature of the thermostat oven;

a buffer container, disposed outside the thermostat oven, containing a buffer solution in which the sample injecting end, from which ends of capillaries protrude, is immersed;

a second temperature controlling part for controlling a temperature of the buffer solution;

a third temperature controlling part for controlling a temperature of the detector part, wherein the first, second, and third temperature controlling parts separately control the temperatures of the thermostat oven, the buffer solution, end the detector part, respectively; and a fourth temperature controlling part for controlling a temperature of a portion of the multi-capillary array disposed between, and in the vicinity of, the thermostat oven and the detector part; and a fifth temperature controlling part capable of controlling a temperature of the multi-capillary array located beyond the detector part;

wherein the first temperature controlling part is capable of controlling a temperature of the thermostat oven separately from the temperature of the multi-capillary array located beyond the detector part and controlled by the fifth temperature controlling part, and the temperature controlling parts are arranged along the electrification part in the direction of the electrophoretic flow beginning with the second temperature controlling part, followed by the first temperature controlling part, followed by the fourth temperature controlling part, followed by the third temperature controlling part.

36. A multi-capillary electrophoresis apparatus comprising:

a multi-capillary array having a plurality of capillaries filled with an isolation medium for isolating a sample, a sample injecting end on one end thereof and a detector part for acquiring information depending on the sample at a position remote from the sample injecting end;

a voltage applying part for applying a voltage to an electrification path between the sample injecting end and the detector part, the voltage driving the sample in a direction of electrophoretic flow along the electrification path from the sample injecting end to a second end;

a thermostat oven containing the multi-capillary array except for portions that extrude from the thermostat oven, wherein the thermostat oven has a first temperature controlling part for controlling a temperature of the thermostat oven;

a buffer container, disposed outside the thermostat oven and containing a buffer solution in which the sample injecting end, from which ends of capillaries protrude, is immersed;

a second temperature controlling part that controls a temperature of the detector separately from the temperature of the thermostat oven controlled by the first temperature controlling part;

a third temperature controlling part for controlling a temperature in the vicinity of the detector part, in between the detector part and the thermostat oven; and a fourth temperature controlling part capable of controlling a temperature of the multi-capillary array located beyond the detector part;

wherein the first temperature controlling part is capable of controlling a temperature of the thermostat oven separately from the temperature of the multi-capillary array located beyond the detector part and controlled by the fourth temperature controlling part, and the temperature controlling parts are arranged along the electrification path in the direction of the electrophoretic flow beginning with the first temperature controlling part, followed by the third temperature controlling part, followed by the second temperature controlling part.

37. A multi-capillary electrophoresis apparatus comprising:

a multi-capillary array having a plurality of capillaries filled with an isolation medium for isolating a sample, a sample injecting end on one end thereof and a detector part for acquiring information depending on the sample at a position remote from the sample injecting end, the detector part being enclosed in a container;

a voltage applying part for applying a voltage to an electrification path between the sample injecting end and the detector part, the voltage driving the sample in a direction of electrophoretic flow along the electrification path from the sample injecting end to a second end opposite the sample injecting end;

a thermostat oven containing the multi-capillary array except for portions that protrude from the thermostat oven, wherein the thermostat oven has a first temperature controlling part for controlling a temperature of the thermostat oven;

a buffer container, disposed outside the thermostat oven, containing a buffer solution whose temperature is controlled, in which the sample injecting end, from which ends of capillaries protrude, is immersed;

a gel block arranged outside the thermostat oven for charging the isolation medium in the capillary array, the gel block being operably connected by a first connection to the multi-capillary array and by a second connection to an isolation medium container, for filling the capillaries of the multi-capillary array with isolation medium from the isolation medium container;

a second temperature controlling part for controlling a temperature of the gel block separately from the temperature of the thermostat oven;

a third temperature controlling part for controlling a temperature of the multi-capillary array located beyond the detector part; and a fourth temperature controlling part for controlling a temperature in a vicinity of an outlet of the thermostat oven on a side of the detector part;

wherein the first temperature controlling part is capable of controlling a temperature of the thermostat oven separately from the temperature of the multi-capillary array located beyond the detector part and controlled by the third temperature controlling part, and the temperature controlling parts are arranged along the electrification path in the direction of the electrophoretic flow beginning with the first temperature controlling part, followed by the third temperature controlling part, followed by the second temperature controlling part.

38. A multi-capillary electrophoresis apparatus comprising:
- a multi-capillary array having a plurality of capillaries filled with an isolation medium for isolating a sample, a sample injecting end on one end thereof, and a detector part for acquiring information depending on the isolated sample at a position remote from the sample injection end;
- a voltage applying part for applying a voltage to an electrification path between the sample injecting end and the detector part;
- a thermostat oven containing the multi-capillary array except for portions of the multi-capillary array that protrude from the thermostat oven, wherein the thermostat oven has a first temperature controlling part for controlling a temperature of the thermostat oven;
- a flow path filled with the isolation medium and connected to the multi-capillary array;
- a buffer container, disposed outside the thermostat oven, containing a buffer solution whose temperature is controlled, in which the sample injecting end, from which ends of capillaries protrude, is immersed;
- a second temperature controlling part for controlling a temperature of the detector part;
- a third temperature controlling part for controlling a temperature of the multi-capillary array located beyond the detector part;
- a fourth temperature controlling part for controlling a temperature of the buffer solution, separately from the temperature of the thermostat oven controlled by the first temperature controlling part, the temperature of the detector part controlled by the second temperature controlling part, and the temperature of the portion of the multi-capillary array located between the detector part and the thermostat oven controlled by the third temperature controlling part; and
- a fifth temperature controlling part for controlling a temperature in a vicinity of an outlet of the thermostat oven on a side of the detector part;
- wherein the first temperature controlling part is capable of controlling a temperature of the thermostat oven, separately from the temperature of the multi-capillary array located beyond the detector part and controlled by the third temperature controlling part.

39. A method of multi-capillary electrophoresis, comprising:
- providing the multi-capillary electrophoresis apparatus of claim 17, immersing the sample injecting end of the multi-capillary array into a buffer solution; conducting an electrophoresis prerun with the sample injecting end of the array immersed in the buffer solution;
- withdrawing the sample injecting end of the array from the buffer solution;
- removing a minor portion of the separation medium from the sample injecting end of the array; and
- immersing the sample injecting end in a sample.

* * * * *

UNITED STATES PATENT AND TRADEMARK OFFICE
CERTIFICATE OF CORRECTION

PATENT NO. : 7,459,068 B2  Page 1 of 1
APPLICATION NO. : 10/309729
DATED : December 2, 2008
INVENTOR(S) : Nordman et al.

It is certified that error appears in the above-identified patent and that said Letters Patent is hereby corrected as shown below:

On the title page:
At item (73) on the front page of the Original Letters Patent, please add the following Assignee after Applied Biosystems Inc., Foster City, CA (US), --; Hitachi High-Technologies Corporation, Ibaragi, Japan (JP)--.

Signed and Sealed this

Thirtieth Day of June, 2009

JOHN DOLL
*Acting Director of the United States Patent and Trademark Office*